United States Patent
Schryver et al.

[11] Patent Number: 5,945,052
[45] Date of Patent: *Aug. 31, 1999

[54] UNITARY "Y" TUBING AND METHOD FOR MANUFACTURING SAME

[75] Inventors: Charles Schryver, Atascadero; David Batdorf, Jr., Paso Robles, both of Calif.

[73] Assignee: Specialty Silicone Fabricators, Paso Robles, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/530,523

[22] Filed: Sep. 18, 1995

[51] Int. Cl.$^6$ ................................................. B29C 47/22
[52] U.S. Cl. .................. 264/167; 264/177.16; 425/381; 425/465; 425/466; 425/467
[58] Field of Search ..................................... 604/264, 280, 604/284; 264/177.13, 177.14, 167, 177.16; 138/118, 177, DIG. 11; 425/381, 465, 466, 467

[56] References Cited

U.S. PATENT DOCUMENTS

| 720,535 | 2/1903 | Schwechler | 425/466 |
|---|---|---|---|
| 1,885,747 | 11/1932 | Maurer | 425/466 |
| 2,503,230 | 4/1950 | Dyer | 425/467 |
| 3,174,364 | 3/1965 | Sims | 425/466 |
| 5,476,453 | 12/1995 | Mehta | 64/281 |

OTHER PUBLICATIONS

ACMI, Catalog of Catheters and Accessories, pp. 63–64, 1960.

*Primary Examiner*—Jan H. Silbaugh
*Assistant Examiner*—Dae Young Lee
*Attorney, Agent, or Firm*—Michael G. Petit

[57] ABSTRACT

An extruded "Y" or bifurcated tube having unitary construction and an extrusion apparatus therefor. The "Y" tube includes three separate tubes, each tube having a central lumen, and a transition portion integral with the tubes and providing physical connection and fluid communication between the individual lumens of the three separate tubes. The first of the three tubes has a first lumen and is first formed by extrusion through a convention extruding die. The extruder die then gradually bifurcates the first tube, providing a gradual transition between the first tube and the second and third tubes. The lumens in the second and third tubes thus formed remain in uninterrupted fluid communication with the lumen of the first tube. The bifurcation takes place with the first tube to form second and third tubes smoothly and over a transition distance which is easily controlled by the extruder die. The bifurcated second and third tubes are continuous with the first tube making the "Y" tube unitary. There are no joints to pull apart or "T" or "Y" connectors between the tubes which may be vulnerable to separation. Moreover, since the extruded bifurcated or "Y" tubing is unitary and the first, second and third tubes may have any desired length without limitation, the extruded bifurcated tubing of the present invention overcomes length limitation on analogous first, second and third tubes imposed by practical engineering considerations operable for molding "Y" tubing.

2 Claims, 4 Drawing Sheets

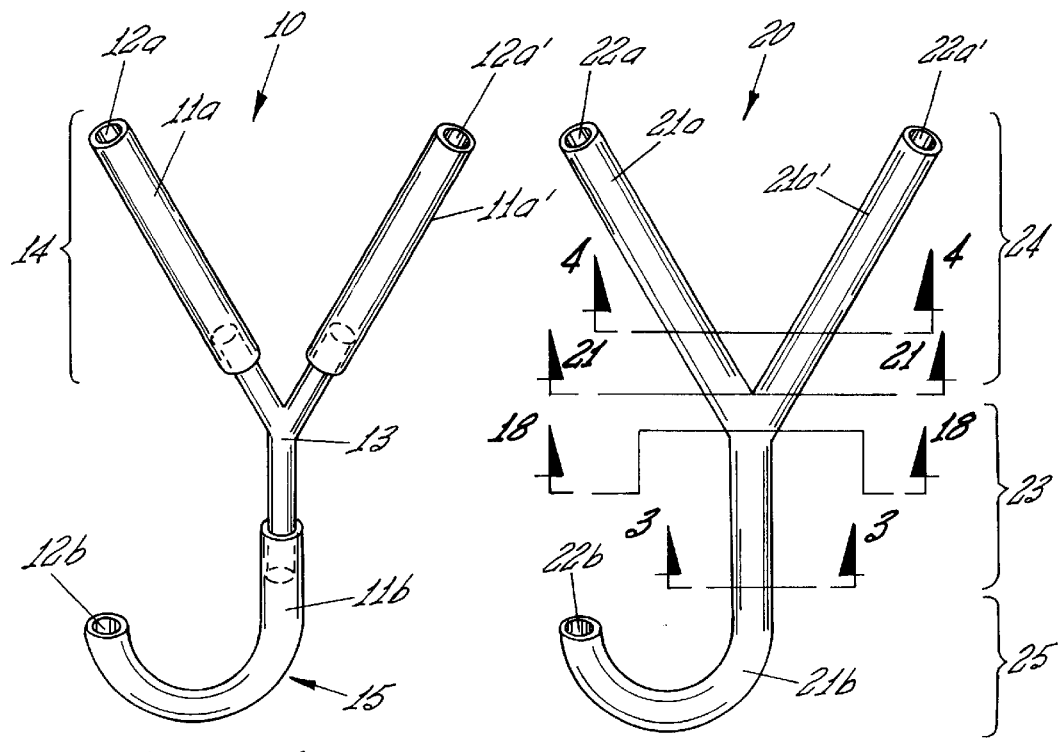
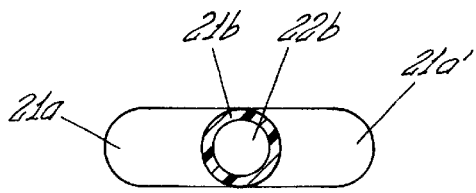
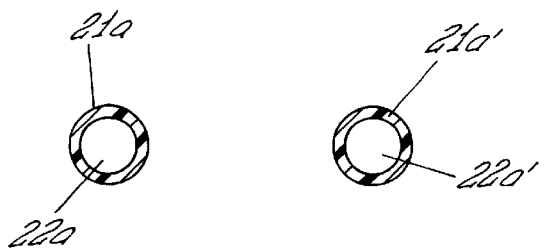

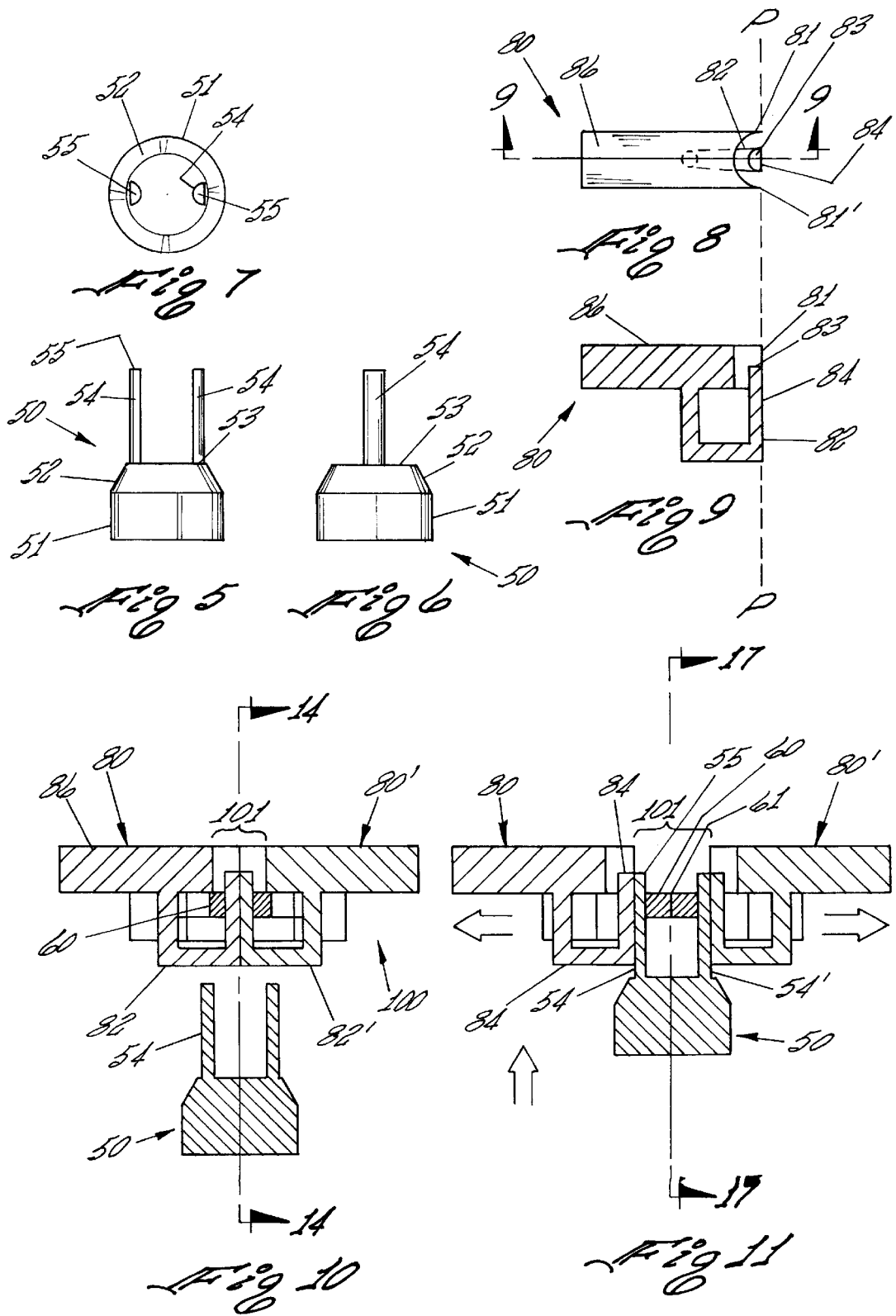

UNITARY "Y" TUBING AND METHOD FOR MANUFACTURING SAME

BACKGROUND OF THE INVENTION

1. Field of the Invention

This invention relates to a unitary bifurcated tubing and an extrusion apparatus for making the same.

2. Prior Art

Bifurcated or "Y" tubing is well known in the art and has many applications. For example, "Y" tubing is commonly found on medical devices such as stethoscopes, drain tubing, intravenous sets, vacuum manifolds and the like. Bifurcated tubing is presently made by one of two processes. The first process involves the use of a "Y" or "T" adapter (usually plastic) which is a (usually molded) article having three tubular arms projecting from a common axis each arm having an inner lumen; each inner lumen being fluidly connected to the inner lumen of the other arms. Means are provided at the distal or terminal end of each of the three "Y" adapter arms for the attachment of tubing to provide a bifurcated tubing assembly. Thus, although the goal of dividing a single tube having a single lumen into two tubes having separate lumens is achieved, the assembly has three structurally weak points where each of the three separate tubes are attached to the arms of the "Y" adapter. The assembled non-unitary bifurcated tubing is vulnerable to separation at these points. Product failure due to separation of a "Y" tube is particularly dangerous when the "Y" or bifurcated tubing is intended to be employed in a medical application such as the intravenous administration of two or more fluid medicaments wherein such separation may result in loss of life.

Molding is another method employed for making bifurcated tubing. Molding has the advantage that it produces a "Y" tubing having unitary construction. The problem with molding is that length of the tubing comprising the "arms" of the "Y" tubing is practically limited by the physical size of the mold in which the "Y" tubing is being produced. Thus, it is not possible to mold a bifurcated tubing having a unitary structure which is not constrained to a particular length by the size of the mold. For certain applications such as distributing or collecting a fluid or tube-transmissible information to and/or from a plurality of locations such size constraints imposed by molding the "Y" tubing may preclude using a unitary bifurcated tubing.

Due to the joint separation problems discussed earlier and wherein a "Y" tube assembly and imposed thereon by connecting separate tubes to a "Y" type adapter, and the limitation due to the practiced restriction on tube length inherent in the molding method of making a "Y" tube, it is desirable to employ extrusion to produce a unitary "Y" tubing which resists separation and can be made in any length.

SUMMARY OF THE INVENTION

It is an object of this invention to provide a bifurcated tubing having unitary construction.

It is another object of this invention to provide a unitary bifurcated tubing means of extrusion.

It is yet another object of this invention to provide an apparatus and method for making a unitary bifurcated or "Y" tubing in any desired length without practical limitation thereon.

The features of the invention believed to be novel are set forth with particularity in the appended claims. However, the invention itself both as to organization and method of operation together with further objects and advantages thereof may best be understood by reference to the following description taken in conjunction with the accompanying drawings in which:

BRIEF DESCRIPTION OF THE DRAWINGS

FIG. 1 is perspective view of a section of bifurcated ("Y") tubing in accordance with the prior art.

FIG. 2 is a perspective view of a section of "Y" tubing in accordance with the present invention.

FIG. 3 is a cross-sectional view of the bifurcated tubing of FIG. 2 along section line 3—3.

FIG. 4 is a cross-sectional view of the bifurcated tubing of the present invention as shown in FIG. 2 along section line 4—4.

FIG. 5 is a side elevational view of a mandrel in accordance with the present invention.

FIG. 6 is a side elevational view of the mandrel in FIG. 5 but viewed at right angles to the view shown in FIG. 5.

FIG. 7 is a top view of the mandrel in accordance with FIG. 5.

FIG. 8 is a top view of a single bridge slide in accordance with the present invention.

FIG. 9 is a cross-sectional view of the bridge slide of FIG. 8 taken along section line 9—9.

FIG. 10 is a side cross-sectional view of an extruder die in accordance with the present invention viewed along the direction of motion of the bifurcating slides.

FIG. 11 is a cross-sectional view of the extruder die of FIG. 10 wherein the mandrel is advanced to partially occlude the die orifice and the bridge slides are retracted.

DESCRIPTION OF THE PREFERRED EMBODIMENTS

Figure 12:
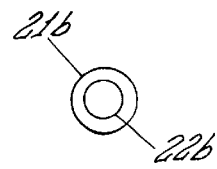
FIG. 12 is a cross-sectional view of an extruded tubing when the elements of the extrusion die are in the position shown in FIG. 13.

Turning first to FIG. 1, in which a bifurcated tubing in accordance with the prior art is shown generally indicated at 10, a substantially inflexible "Y" adapter 13 is employed to couple three discrete single lumen tubing 11a, 11a' and 11b together. The discrete tubes 11a and 11a' each have a central lumen 12a and 12a' therein. The portion of the bifurcated tubing, tubes 11a and 11a', can be referred to as the bifurcated portion 14 (or 24 in FIG. 2). The opposite single tube 11b is referred to herein as the single lumen portion 15 (or 25 in FIG. 2) of the bifurcated or "Y" tubing 10 or 20. The "Y" adapter 13 is, of course, also a "Y" tubing but is normally made from molded plastic and is rigid and constrained in size by the dimensions of the mold in which it is made.

In FIG. 2, a "Y" tubing is shown in which a bifurcation transition, generally indicated at 23, includes an internal division of the single lumen portion 25 to form a bifurcated portion 24. The advantage of the "Y" tubing 20 is that it requires no coupling adapter between the bifurcated portion 24 and the single lumen portion 25 thereby imparting a structural integrity to the "Y" tubing 20 that is missing in the prior art "Y" tubing 10.

FIG. 3 is a cross-sectional view of the "Y" tubing 20 along section line 3-3 of FIG. 2. In FIG. 3, the single lumen portion 25 of the "Y" tubing 20 consists of a tube 21b having a center lumen 22b. The bifurcated portions of the "Y" tubing 20 consists of two tubes 21a and 21a' each having a central lumens 22a and 22a' which are in fluid communication with the lumen 22b of the single lumen portion 21b.

In FIG. 4, a cross-sectional view of the "Y" tubing 20 of FIG. 2 is shown along section line 4—4. In order to effect the transition from an extruded tubing having the cross-sectional view of FIG. 3 to an extruded tubing having the cross-sectional view of FIG. 4 and, at the same time, provide continuous fluid communication between the lumen 22b and the lumens 22a and 22a', a novel extruder die was constructed.

The extruder die consists of three distinct elements: a pair of bridge slides, a pair of bifurcated slides and a moveable mandrel. The first element of the extruder die is the moveable mandrel generally indicated at 50 in FIG. 5 and FIG. 6. The mandrel 50 comprises a cylindrical portion 51 with a conical beveled portion 52 having a circular flat top 53. Mounted on and projecting upward from the flat top 53 of the beveled portion 52 is a pair of mandrel extensions 54 consisting of two hemicylinders, each hemicylinder having a semicircular cross-section. The hemicylindrical extension portions 54 of the mandrel 50 terminate in a flat top 55. The top 55 is a planar surface having the shape of a semicircle. This is seen more clearly in FIG. 7 which is a top view of the mandrel of FIG. 5. Projecting upward from the flat top 53 are the semicylindrical extensions 54 of the mandrel. The radius of curvature of the semicircles is equal to the radius of lumens 21a, 21a' and 22b which are equal in size. These hemicylindrical portions 54 will alternatively be referred to hereinthroughout as "mandrel extensions" or simply as "mandrel tines."

The second element of the extruder die is a mirror image pair of bridge slides 80. A top view of a single bridge slide 80 is shown in FIG. 8 looking in the direction of the flow stream. The bridge slide 80 comprises a substantially flat rectangular base portion having an arcuate end 85 which consists of an inwardly concave semicircular indentation in the arcuate end of the base portion wherein the diameter of the semicircular indentation is equal to the outer diameter of the extruded tubes 21a, 21a' and 21b which diameters are all equal. The arcuate end 85 has two sharp lateral projections 81 and 81' extending therefrom. A bridge slide tine 82 projects from the bottom of the bridge slide 80, makes a right angle turn and extends forward to a plane P which plane P is parallel to the direction of the flow stream and perpendicular to the flat upper surface 86 of the bridge slide 80 and intersects the two sharp projections 81 and 81' on the arcuate end 85. The bridge slide tine 82 then makes another right angle turn and a semicylindrical portion on the end of the tine ascends to project within the arcuate portion 85 of the bridge slide 80. This is shown more clearly in FIG. 9 where the bridge slide tine 82 is shown ascending to terminate in the plane 86 of the bridge slide 80. The terminal end of the bridge slide tine 82, which terminal end projects into the plane of the flat upper surface 86 within the semicircular indentation has a semicircular cross-section as shown in 84 which is complimentary to the semicircular cross-section of the mandrel tine.

Turning now to FIG. 10 an extruder die in accordance with the present invention is shown. An extruder apparatus (not shown) consists of a chamber having an inlet port operable for conducting a pressurized extrudable material into the chamber, and an extruder die orifice 101 through which the pressurized extrudable material within the chamber is forced to emerge in a direction defining a flow stream. The orientation of the extruder die orifice is in a plane perpendicular to the direction of the flow stream. The particular shape of the extrusion die orifice 101 is determined by the particular spacial arrangement of the moveable extrusion die elements acting cooperatively with each other. Thus, the shape of an extruded article may be altered by manipulating the spatial relationship of the moveable extrusion die elements to vary the cross section of the extruder die orifice. In the present case the moveable extrusion die elements are: (a) the moveable mandrel 50; (b) a pair of bridge slides 80 mounted within the chamber operable to reciprocally slide and oriented with respect to each other so that each of the pair of bridge slides is the mirror image of the other bridge slide; (c) a die orifice 101 lying within a plane; and (d) a pair of bifurcated slides 60 and 61 slideably mounted to reciprocally slide in a plane parallel to the plane of the die orifice 101.

In FIG. 10, the extruder die 100 has the bridge slide slides 80 and 80' fully advanced toward the center of the die orifice 101. When the bridge slides 80 and 80' are fully advanced, the elongate flat surface of the bridge slide tines 82 and 82' are flush against one another so that the flat surfaces of the respected hemicylinders are in juxtaposition. One of the bifurcating slides 60 is only partially shown (because it is behind the pair ofjuxtaposed bridge slide extensions 82 and 82') but is withdrawn so that the pointed tips 61 and 61' (see FIG. 13') are fully retracted from the center of the die orifice 101. The mandrel 50 is also withdrawn from the die orifice 101 so that the mandrel tines 54 do not project into the die orifice 101. This is the position of the die elements when a single lumen tubing is to be extruded through the die orifice 101.

In FIG. 11, the spatial positions of the each of the extrusion die elements has been adjusted to produce an extruded article comprising two tubes each having a separate lumen. The bridge slides 80 and 80' are moved apart in the direction indicated by the broad arrows A and A' respectively thereby moving the bridge slide tines 84 and 84' apart from each other. The mandrel 50 is advanced into the die orifice 101 in the direction of the flow (see arrow B) so that the flat surfaces of the semicylindrical mandrel extensions 54 and 54' are flush with the elongate flat surfaces of the bridge slide tines 84 and 84' respective. The juxtaposition of the hemi-cylinders 84 and 54 and 84' and 54' produce two circular structures partially obstructing the die orifice 101. Thus, tubing extruded by forcing material through the die orifice 101 in the direction of flow will have two lumens therein, each lumen formed by one of the bridge slide tine-mandrel extension pairs. The bifurcation slide 60 and 60' which is shown more clearly in FIGS. 13–16, are advanced into the die orifice until the points 61 and 61' touch thereby dividing the die orifice 101 into the two flow channels and bifurcating the double lumen tubing to form two individual tubes each having a separate lumen.

Figure 13:
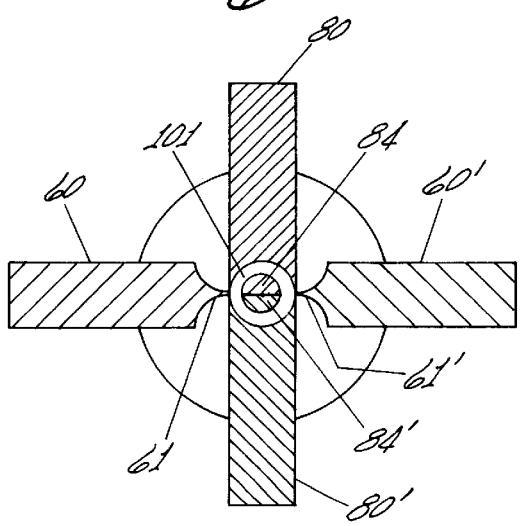
FIG. 13 shows the position of the various portions of the extrusion die in accordance with the present invention during extrusion of the first tube (to be bifurcated).
Figure 14:
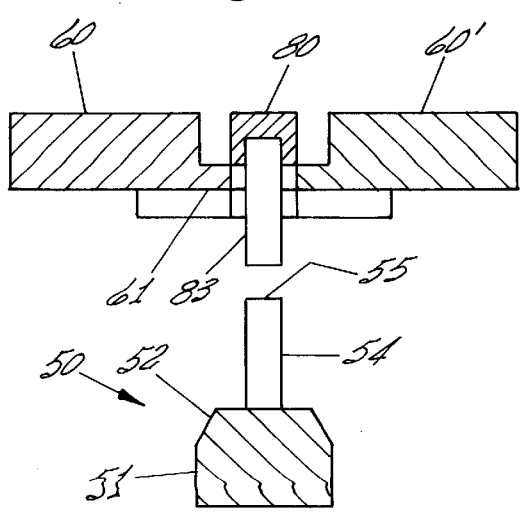
FIG. 14 is a cross-sectional view of FIG. 13 showing the position of the mandrel with respect to the die orifice during extrusion of the tubing shown in cross-section in FIG. 12.

The exact position of each of the elements of the extrusion die during actual extrusion of the bifurcated tubing is shown in the following figures. FIG. 12 is a cross-section of the extruded tubing 21b having a lumen 22b when the elements of the extrusion die are in the position as shown in FIGS. 13 and 14. FIG. 13 is a view of the die orifice when viewed from the exterior of the chamber along the axis defined by the direction of the flow. It is seen that the bifurcation slides 60 and 60' are withdrawn from the die orifice 101. The bridge slides 80 and 80' are advanced so that the elongate flat surface of the bridge slide extension tines 84 and 84' are in juxtaposition and form a cylindrical rod which obstructs the center of the die orifice 101 to form a central lumen 22b in the tubing 21b. The arrangement of elements is seen in side view in FIG. 14. The mandrel 50 is shown fully retracted from the die orifice so that the mandrel tine 54 and 54' do not project thereinto.

Figure 15:
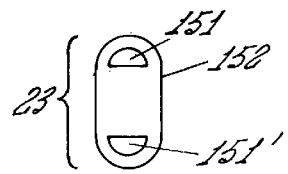
FIG. 15 is a cross-sectional view of a tubing extruded through the die orifice when the elements comprising the extrusion die are in the position indicated in FIG. 16.
Figure 16:
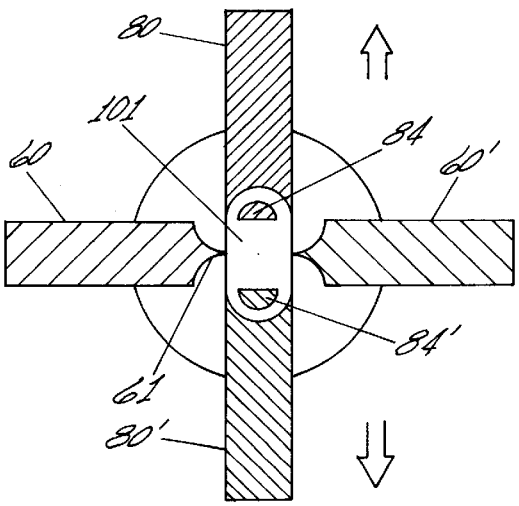
FIG. 16 is a top view of the position of the elements comprising the extrusion die during extrusion of tubing having the cross-section as shown in FIG. 15.
Figure 17:
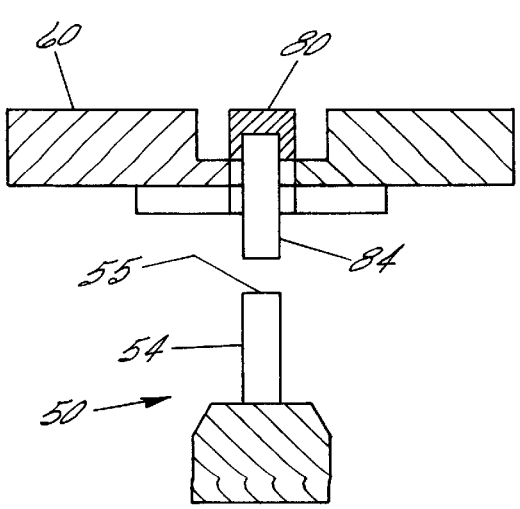
FIG. 17 is a side view of the extrusion die of FIG. 16 showing the bridge slides retracted and with the mandrel remaining withdrawn from within the die orifice.
Figure 18:
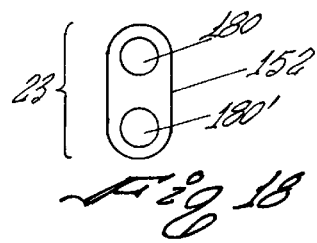
FIG. 18 is a cross-sectional view of an extruded tubing when the moveable elements of the extruder die are in the position shown in FIGS. 19 and 20.
Figure 21:
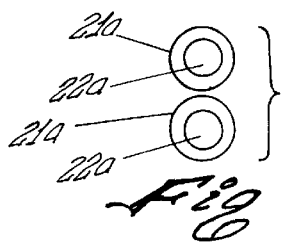
FIG. 21 is a cross-sectional view of tubing extruded through the die orifice when the elements of the extrusion die are the position as shown in FIGS. 22 and 23.

In FIG. 15, an extruded double lumen tubing 152 is shown. The shape of the two lumens 151 and 151' are seen to be semicircular in cross-section because they are formed by the bridge slide tines 83 and 83'. Two cross-sectional views of the bifurcation transition 23 portion of the bifurcated tubing 20 between the single lumen portion 25 and the bifurcated portion 24 of the bifurcated 20 is shown in FIGS. 15, 18 and 21. It is seen that the lumens 151 and 151' and the tubing 152 are in transition and have a semicircular cross-section corresponding to the semicircular cross-section 83 of the bridge slide tines 84 and 84'. This cross-section is generated by the spatial positioning of the extrusion die elements as shown in FIG. 16. The bridge slides 80 and 80' are withdrawn in the directions defined by A—A' and the bifurcation slide 60 and 60' are in the same positions as shown in FIG. 13. As shown in FIG. 17, the mandrel remains in the same position as shown in FIG. 14. Thus, to generate an extruded tubing having the cross-section shown in FIG. 15, the elements of the extrusion die remain in the same position as for FIG. 12 except that the bridge slides 80 and 80' are fully retracted from the center of the die orifice 101 in the direction of the broad arrows A and A' respectively from the die orifice 101.

Figure 19:
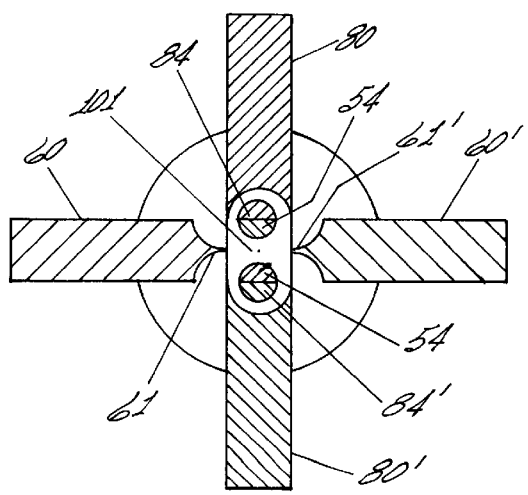
FIG. 19 is a top view of the extruder die in accordance with the present invention showing the positional relationship of the slides and mandrel during extrusion of the tubing having a cross-section shown in FIG. 18.

FIG. 18 shows an extruded tubing 152 having two discrete circular lumens 180 and 180'. FIG. 18 is a cross-sectional view of the bifurcation transition 23 of the "Y" tubing shown in FIG. 2 along section line 18—18. To produce an extruded tubing having the cross-section shown in FIG. 18, the bridge slides 80 and 80' are retracted from the center of the die orifice as before. The bifurcation slides 60 and 60' remain fully retracted from the center of the die orifice 101 as shown. In FIG. 19, the mandrel 50 (not shown) advanced in the direction of flow into the die orifice 101 so that the mandrel tines 54 slidingly engage the bridge slide extension tines 84. Thus, the double lumens 180 and 180' are circular due to the juxtaposition of the bridge slide tines 84 and 84' and the mandrel tines 54 and 54' respectively but the outer surface of the tubing 152 is oval in shape because the bifurcation slide 60 60' are still withdrawn.

Figure 22:
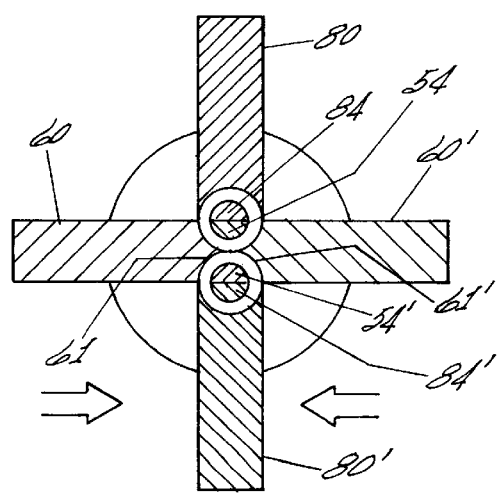
FIG. 22 shows the position of the slides and mandrel of the extruder die in accordance with the present invention with the bifurcating slides advanced to abut in the center of the die orifice to split the double lumen tubing into second and third tubes.
Figure 20:
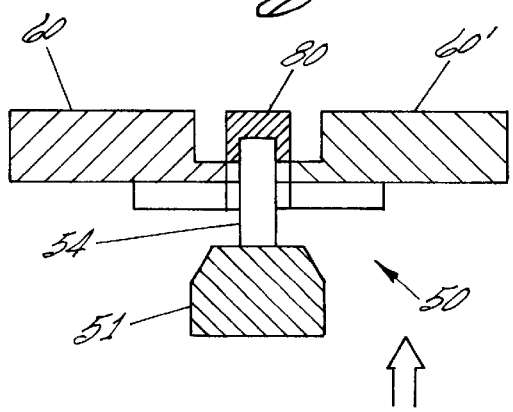
FIG. 20 is a cross-sectional view of the extrusion die of FIG. 19 showing the mandrel advanced into the die orifice so that the flat surface of the mandrel's hemicylindrical extensions abut the mating surfaces of the bridge slides tines.
Figure 23:
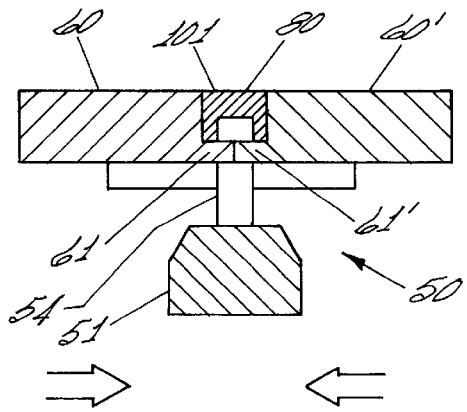
FIG. 23 shows in cross-section the extrusion die of FIG. 22 wherein the mandrel is fully advanced and the bifurcating slides are fully advanced to touch one another at the point of separation of the extruded tube.

A bifurcated tubing 21 comprising two distinct tubes 21a and 21a' having lumens 22a and 22a' and shown in cross-section in FIG. 21, is generated by the arrangement of extrusion die elements as shown in FIG. 22. The lumens 22a and 22a' are formed by the pairing and juxtaposition of the hemicylindrical slide extension tines and the mandrel tines. The outer surface of the tubes 21a and 21a' are round because the bifurcation slide 60 and 60' have been advanced so that the points 61 and 61' touch thereby creating a pair of circular apertures defining the outer surface of tubing extruded therethrough. The arrangement of elements is shown in vertical cross-section FIG. 23. In FIG. 23, the bifurcation slides 60 and 60' are fully advanced into the die orifice 101 in the direction of the broad arrows B and B' until the points 61 and 61' touch, the bridge slides 80 and 80' remain retracted and the mandrel 50 is advanced fully into the die orifice 101 causing the mandrel extension tines 54 and 54' to matingly engage the bridge slide tines 84 and 84'.

The bifurcating slides 60 and 60' are slidably mounted adjacent to the die orifice 101 in a plane parallel to the plane of the die orifice 10. Means are provided for moving the bifurcating slides reciprocally along a first axis. Such means are preferably a motor driven cam as is commonly employed in the art. The bridge slides 80 and 80' are similarly slidingly mounted adjacent to the die orifice 101 in a plane parallel to the plane of the die orifice to move reciprocally in a direction along a second axis which is perpendicular to the first axis. The mandrel is mounted to move reciprocally in and out of the die orifice along the direction of flow.

While particular embodiments of the present invention have been illustrated and described it would be obvious to those skilled in the art that various other changes and modifications can be made without departing from the spirit and scope of the invention. It is therefore intended to cover in the pending claims all such changes and modifications that are within the scope of this invention.

What we claim is:

1. A method for forming an extruded bifurcated tubing having a unitary construction with an undivided tube portion having a first lumen therewithin, a divided tube portion comprising two tubes each having second lumens therewithin, and a double lumen transition portion positioned between said undivided tube portion and said divided tube portion, wherein said first lumen and said second lumens are in fluid communication with each other through said double lumen transition portion, said method being adapted to form extruded bifurcated tubing having an undivided tube portion and divided tube portions of any desired length, comprising the following steps:

(a) providing an extrusion die comprising a chamber having an inlet port operable for conducting a pressurized extrudable material into said chamber and an extrusion die orifice comprising an opening in said chamber providing means for conducting the pressurized extrudable material out of said chamber in a direction defining a flowstream, and wherein the shape of said extrusion die orifice is controlled by adjustable shaping means disposed within said chamber, said adjustable shaping means comprising; (1) two identical bridge slides operable for controlling the outer dimension of the extrusion die orifice disposed in mirror image opposition to one another and slideably mounted to move reciprocally forward and away from one another in a first direction perpendicular to the direction of the flowstream, and wherein each bridge slide comprises a substantially planar base plate having a concave semicircular indentation in one end thereof and an extension portion projecting from said base plate at least a portion of which comprises a semicylinder projecting into said concave semicircular indentation, said extension portions being adapted to form lumens in said tubing; (2) two identical bifurcating slides slidingly mounted in mirror image opposition to one another and adapted to move toward and away from each other in a second direction which second direction is orthogonal to both the direction of the flowstream and said first direction, each of said bifurcating slides comprising an elongate plate having a bifurcating tip on one end thereof and wherein said bifurcating tips are in juxtaposition when said bifurcating slides are advanced toward one another, and (3) a mandrel element slideably mounted to move in the direction of the flowstream comprising a support member having two semicylindrical elements projecting therefrom;

(b) bringing the ends of the bridge slides with concave semicircular indentations and extension portions into juxtaposition with each other to form to the desired outer dimension and desired inner lumen dimension of the undivided tube portion;

(c) forcing an extrudable material through the inlet port of the die and into the die chamber, which extrudable material will flow out the chamber through the extrusion die orifice in a direction defining a flowstream, to form the undivided tube portion;

(d) moving the ends of the bridge slides apart and advancing the extrusion die mandrel in the direction of the flowstream to create the double lumen transition portion;

(e) sliding the bifurcating slides together in a plane orthogonal to said direction defining a flowstream to divide the transition portion into the divided tube portion with two tubes each having second lumens.

2. A method for forming an extruded bifurcated tubing having a unitary construction with an undivided tube portion having a first lumen therewithin, a divided tube portion comprising two tubes each having second lumens therewithin, and a double lumen transition portion positioned between said undivided tube portion and said divided tube portion, wherein said first lumen and said second lumens are in fluid communication with each other through said double lumen transition portion, said method being adapted to form extruded bifurcated tubing having an undivided tube portion and divided tube portions of any desired length, comprising the following steps:

(a) providing an extrusion die comprising a chamber having an inlet port operable for conducting a pressurized extrudable material into said chamber and an extrusion die orifice comprising an opening in said chamber providing means for conducting the pressurized extrudable material out of said chamber in a direction defining a flowstream, and wherein the shape of said extrusion die orifice is controlled by adjustable shaping means disposed within said chamber, said adjustable shaping means comprising; (1) two identical bridge slides operable for controlling the outer dimension of the extrusion die orifice disposed in mirror image opposition to one another and slideably mounted to move reciprocally forward and away from one another in a first direction perpendicular to the direction of the flowstream, and wherein each bridge slide comprises a substantially planar base plate having a concave semicircular indentation in one end thereof and an extension portion projecting from said base plate at least a portion of which comprises a semi-cylinder projecting into said concave semicircular indentation, said extension portions being adapted to form lumens in said tubing; (2) two identical bifurcating slides slidingly mounted in mirror image opposition to one another and adapted to move toward and away from each other in a second direction which second direction is orthogonal to both the direction of the flowstream and said first direction, each of said bifurcating slides comprising an elongate plate having a bifurcating tip on one end thereof and wherein said bifurcating tips are in juxtaposition when said bifurcating slides are advanced toward one another, and (3) a mandrel element slideably mounted to move in the direction of the flowstream comprising a support member having two semicylindrical elements projecting therefrom;

(b) bringing the ends of the bridge slides with concave semicircular indentations and extension portions into juxtaposition with each other to form to the desired outer dimension and desired inner lumen dimension of the undivided tube portion;

(c) forcing an extrudable material through the inlet port of the die and into the die chamber, which extrudable material will flow out the chamber through the extrusion die orifice in a direction defining a flowstream, to form the undivided tube portion;

(d) moving the ends of the bridge slides apart and advancing the extrusion die mandrel in the direction of the flowstream to create the double lumen transition portion;

(e) sliding the bifurcating slides together in a plane orthogonal to said direction defining a flowstream to divide the transition portion into the divided tube portion with two tubes each having second lumens.

* * * * *